United States Patent [19]

Garwood et al.

[11] 4,150,062

[45] Apr. 17, 1979

[54] LIGHT OLEFIN PROCESSING

[75] Inventors: William E. Garwood, Haddonfield; Philip D. Caesar, Princeton; James A. Brennan, Cherry Hill, all of N.J.

[73] Assignee: Mobil Oil Corporation, New York, N.Y.

[21] Appl. No.: 889,486

[22] Filed: Mar. 23, 1978

Related U.S. Application Data

[63] Continuation of Ser. No. 752,718, Dec. 20, 1976, abandoned.

[51] Int. Cl.$^2$ .................. C07C 15/02; B01J 29/28
[52] U.S. Cl. .................. 260/673; 208/DIG. 2; 208/71; 260/668 R; 260/676 R; 260/677 R; 260/683.15 R; 260/683.15 A
[58] Field of Search .......................... 260/673

[56] References Cited

U.S. PATENT DOCUMENTS

| | | | |
|---|---|---|---|
| 3,760,024 | 9/1973 | Cattanach | 260/673 |
| 3,894,102 | 7/1975 | Chang et al. | 260/668 R |
| 3,907,663 | 9/1975 | Owen | 208/70 |
| 3,928,483 | 12/1975 | Chang et al. | 260/668 R |
| 4,012,455 | 3/1977 | Owen et al. | 260/668 R |

Primary Examiner—Delbert E. Gantz
Assistant Examiner—G. E. Schmitkons
Attorney, Agent, or Firm—Charles A. Huggett; Michael G. Gilman; Charles J. Speciale

[57] ABSTRACT

An improved processing technique is provided for conversion of olefins of 2 to 4 carbon atoms to product comprising high octane gasoline components. Embodiments of the present improved processing technique include conversion of light olefins to high octane olefinic gasoline components, and conversion of light olefins to high octane aromatic gasoline components.

The improved technique comprises contacting an appropriate light olefin feedstock with a catalyst comprising a crystalline aluminosilicate zeolite characterized by a silica/alumina mole ratio of at least 12 and a constraint index, hereinafter defined, within the approximate range of 1 to 12 in the presence of a relatively large amount of co-fed water. The amount of co-fed water is maintained at from about 0.5 to about 15 moles of water/mole of olefin feedstock.

48 Claims, 1 Drawing Figure

LIGHT OLEFIN PROCESSING

CROSS REFERENCE TO RELATED APPLICATION

This is a continuation of application Ser. No. 752,718 filed Dec. 20, 1976, and now abandoned.

BACKGROUND OF THE INVENTION

1. Field of the Invention

This invention relates to manufacturing gasoline. It more particularly refers to an improved technique for upgrading relatively low octane number feed stocks to products of substantially higher octane number and therefore of substantially greater economic value.

2. Description of Prior Art

Trace amounts of water used to promote various catalytic reactions, not including production of high octane gasoline components by way of olefination or aromatization, is known to the art. For example, U.S. Pat. No. 3,546,100 teaches restricting the partial pressure of water in contact with a hydrocracking catalyst during hydrocracking of a hydrocarbon compound to within the range of 10 to 130 mm. U.S. Pat. No. 3,649,524 teaches a high temperature reforming process using only 8–20 ppm water.

Somewhat larger amounts of water have been used in high temperature catalytic dehydrogenation of hydrocarbons (U.S. Pat. No. 3,907,921), wherein 25–3000 ppm of water is used; and in hydrodesulfurization of gas oils and cycle oils (U.S. Pat. No. 3,720,602), wherein 5 to 50 percent of water is injected. In the latter patent, the catalyst material used does not include zeolite materials.

The use of large amounts of water, i.e. about 0.5 to about 16 moles water/mole hydrocarbon feedstock, would be expected, based upon the teaching of the art, to destroy conventional porous, siliceous heterogeneous catalysts, such as used in the present method.

U.S. Pat. No. 3,760,024 discloses an aromatization process for a feedstock comprising $C_2$ to $C_4$ paraffins and olefins comprising contacting such feedstock with a crystalline aluminosilicate of the ZSM-5 type at a temperature of about 200° to 1400° F., in the absence of added hydrogen, at pressures of about 0 to 1000 psig, and space velocities equivalent to about 0.1 to 500 WHSV. U.S. Pat. No. 3,756,942 discloses contacting a feedstock having a boiling range of $C_5$ to those fractions wherein at least 50 volume percent boils no higher than 250° F., with a crystalline aluminosilicate zeolite of the ZSM-5 type at a space velocity equivalent to about 1 to 15 WHSV, a pressure up to about 35 atmospheres and a temperature of about 650° to 1500° F. No water is used in either of these methods.

SUMMARY OF THE INVENTION

This invention relates to improved processing of light olefins of from 2 to 4 carbon atoms to product comprising high octane gasoline components wherein said processing comprises contacting such an olefin feedstock in the presence of from about 0.5 to about 15 moles of co-fed water/mole of olefin feedstock with a catalyst comprising a crystalline aluminosilicate zeolite characterized by a silica/alumina mole ratio of at least 12 and a constraint index, hereinafter defined, within the approximate range of 1 to 12.

The crystalline aluminosilicate zeolites used in the catalyst composition of the process of this invention are referred to generally as ZSM-5 type or as behaving like ZSM-5 and include ZSM-5, ZSM-11, ZSM-12, ZSM-35 and ZSM-38, specifically described hereinafter.

DESCRIPTION OF SPECIFIC EMBODIMENTS

The catalyst composition useful in this invention comprises a crystalline aluminosilicate zeolite characterized by a silica/alumina mole ratio of at least 12 and a constraint index of from about 1 to about 12, non-limiting examples of which include ZSM-5, ZSM-11, ZSM-12, ZSM-35 and ZSM-38.

Zeolite ZSM-5 is taught by U.S. Pat. No. 3,702,886, issued Nov. 14, 1972, the disclosure of which is incorporated herein by reference. In a preferred synthesized form, the zeolite ZSM-5 for use in the catalyst composition useful in this invention has a formula, in terms of mole ratios of oxides in anhydrous state, as follows:

$$(0.9 \pm 0.2)M_{2/n}O:Al_2O_3:xSiO_2$$

wherein M is selected from the group consisting of a mixture of alkali metal cations, especially sodium, and tetraalkylammonium cations, the alkyl groups of which preferably contain 2 to 5 carbon atoms, and x is at least 5. Particularly preferred is a zeolite having the formula in the anhydrous state as follows:

$$(0.9 \pm 0.2)M_{2/n}O:Al_2O_3:ZSiO_2$$

wherein Z is from greater than 30 to about 350 or higher.

Zeolite ZSM-11 is taught by U.S. Pat. No. 3,709,979, issued Jan. 19, 1973, the disclosure of which is incorporated herein by reference. In the as synthesized form, the zeolite ZSM-11 for use in the catalyst composition useful in this invention has a formula, in terms of mole ratios of oxides in the anhydrous state, as follows:

$$(0.9 \pm 0.3)M_{2/n}O:Al_2O_3:20 \text{ to } 90 \text{ } SiO_2$$

wherein M is a mixture of at least one of the quaternary cations of a Group V-A element of the Periodic Table and alkali metal cations, especially sodium. The original cations can be present so that the amount of quaternary metal cations is between 10 and 90 percent of the total amount of the original cations. Thus, the zeolite can be expressed by the following formula in terms of mole ratios of oxides:

$$(0.9 \pm 0.3)(xXR_4 + 1 - xM_{2/n}O):Al_2O_3:20 \text{ to } 90 \text{ } SiO_2$$

wherein R is an alkyl or aryl group having between 1 and 7 carbon atoms, M is an alkali metal cation, X is a group V-A element, especially a metal, and x is between 0.1 and 0.9.

Zeolite ZSM-12 is taught by U.S. Pat. No. 3,832,449, issued Aug. 27, 1974, the disclosure of which is incorporated hereby by reference.

ZSM-35 is described in U.S. application Ser. No. 528,061, filed Nov. 29, 1974 (now U.S. Pat. No. 4,016,245). This zeolite can be identified, in terms of mole ratios of oxides and in the anhydrous state, as follows:

wherein R is an organic nitrogen-containing cation derived from ethylenediamine or pyrrolidine, M is an alkali metal cation and x is greater than 8, and is characterized by a specified X-ray powder diffraction pattern.

In a preferred synthesized form, zeolite ZSM-35 has a formula, in terms of mole ratios of oxides and in the anhydrous state, as follows:

wherein R is an organic nitrogen-containing cation derived from ethylenediamine or pyrrolidine, M is an alkali metal, especially sodium, and y is from greater than 8 to about 50.

ZSM-38 is described in U.S. application Ser. No. 560,412, filed Mar. 20, 1975 (now U.S. Pat. No. 4,046,859). This zeolite can be identified, in terms of mole ratios of oxides and in the anhydrous state, as follows:

wherein R is an organic nitrogen-containing cation derived from a 2-(hydroxyalkyl) trialkylammonium compound, x is greater than 8 and M is an alkali metal cation, and is characterized by a specified X-ray powder diffraction pattern.

In a preferred synthesized form, the zeolite has a formula, in terms of mole ratios of oxides and in the anhydrous state, as follows:

wherein R is an organic nitrogen-containing cation derived from a 2-(hydroxyalkyl) trialkylammonium compound, wherein alkyl is methyl, ethyl or a combination thereof, M is an alkali metal, especially sodium, and y is from greater than 8 to about 50.

Although the zeolites herein described have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of the zeolites for use herein is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anoinic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms, or, if elliptical in pore shape, at least the size of the pores in ZSM-5. In addition, the structure must provide constrained access to larger molecules. It is sometimes possible to judge from a known crystal structure whether such constrained access exists. For example, if the only pore windows in a crystal are fomred by 8-membered rings of oxygen atoms, then access to molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions. Also, structures can be conceived due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12.

Constraint Index (CI) values for some typical catalysts, including those useful herein, are:

| Crystalline Aluminosilicate | CI |
|---|---|
| ZSM-5 | 8.3 |
| ZSM-11 | 8.7 |
| ZSM-12 | 2 |
| ZSM-35 | 2 |
| ZSM-38 | 2 |
| Beta | 0.6 |
| ZSM-4 | 0.5 |
| H-Zeolon | 0.5 |
| REY | 0.4 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The specific zeolites described, when prepared in the presence of organic cations, are catalytically inactive, possibly because the intracrystalline free space is occupied by organic cations from the forming solution. They may be activated by heating, for example, in an inert atmosphere at 1000° F. for one hour, followed by base exchange with ammonium salts and by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours. Before calcination, ammonium cations may be replaced, at least in part, by ion exchange with salts of zinc, nickel, potassium, rate earth metals and the like in accordance with techniques well known in the art.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired for the present process. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolite is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Members of the above group of zeolites for use in the catalyst composition of the present invention possess definite distinguishing crystalline structures as evidenced by the above U.S. Patents incorporated herein by reference.

The synthetic ZSM-35 zeolite possessess a definite distinguishing crystalline structure whose X-ray diffraction pattern shows substantially the significant lines set forth in Table 1.

TABLE 1

| Interplanar Spacing | Relative Intensity |
|---|---|
| 9.6 ± 0.20 | Very Strong-Very, Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |

TABLE 1-continued

| Interplanar Spacing | Relative Intensity |
|---|---|
| 4.58 ± 0.09 | Weak |
| 3.99 ± 0.08 | Strong |
| 3.94 ± 0.08 | Medium-Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak-Medium |
| 3.14 ± 0.06 | Weak-Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

The synthetic ZSM-38 zeolite possesses a definite distinguishing crystalline structure whose X-ray diffraction patterns shows substantially the significant lines set forth in Table 1A.

TABLE 1A

| Interplanar Spacing | Relative Intensity |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

These values were determined by standard technique. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100 I/I_o$, where $I_o$ is the intensity of the strongest line or peak, and k (obs.), the interplanar spacing in Angstrom units, corresponding to the recorded lines, were calculated. It should be understood that these X-ray diffraction patterns are characteristic of all the species of the above respectively identified zeolites. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

Zeolites ZSM-5, ZSM-11 and ZSM-12 for use in the process of this invention are prepared as indicated in their respective patents, incorporated herein by reference above.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 2

| | Broad | Preferred |
|---|---|---|
| $\dfrac{R^+}{R^+ + M^+}$ | 0.02–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° F. to about 400° F. for a period of time of from about 6 hours to about 100 days. A more preferred temperature range is from about 150° F. to about 400° F. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

TABLE 3

| | Broad | Preferred |
|---|---|---|
| $\dfrac{R^+}{R^+ + M^+}$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90° F. to about 400° F. for a period of time of from about 6 hours to about 100 days. A more preferred temperature range is from about 150° F. to about 400° F. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

For the improved process of this invention the suitable zeolite catalyst is employed in combination with a support or binder material such as, for example, a porous inorganic oxide support or a clay binder. Nonlimiting examples of such binder materials include alumina, zirconia, silica, magnesia, thoria, titania, boria and combinations thereof, generally in the form of dried inorganic oxide gels and gelatinous precipitates. Suitable clay materials include, by way of example, bentonite and kieselguhr. The relative proportion of suitable crystalline aluminosilicate zeolite of the total composition of catalyst and binder or support may vary widely with the zeolite content ranging from between about 30 to about 90 percent by weight and more usually in the range of about 50 to about 80 percent by weight of the composition.

Operating conditions employed in the process of the present invention are critical. Such conditions as temperature, pressure, space velocity, molar ratio of co-fed water to olefin reactants, absence of added hydrogen, and the presence of any diluents will have important affects on the process.

The process of this invention is conducted such that conversion of light olefin feedstock is carried out in the vapor-phase by contact in a reaction zone, such as, for example, a fixed bed of catalyst composition, under conversion effective conditions, said catalyst composition being characterized, as synthesized, as comprising one or more of the above-defined zeolite compositions. This process may be conducted in either batch or fluid bed operation with attendant benefits of either operation readily obtainable.

The present improved process may be carried out at a temperature between about 450° F. and 800° F., preferably from about 550° F. to about 750° F., and at pressures ranging from about atmospheric up to about 1000 psig, preferably from about atmospheric to about 450 psig. The weight hourly space velocity (WHSV) may be maintained at from about 0.2 $hr^{-1}$ to about 20 $hr^{-1}$, preferably from about 0.5 $hr^{-1}$ to about 4 $hr^{-1}$. The preferred amount of co-fed water is from about 0.5 to about 5 moles of water/mole of olefin feedstock. Within these limits the conditions of temperature and pressure will vary considerably depending upon equilibrium considerations, exact feed material, and presence or absence of diluents, such as, for example, $C_1$-$C_4$ paraffins, such as methane, ethane, propane, isobutane and n-butane; and hydrogen sulfide. Optimum conditions are those in which maximum yields of desired high octane gasoline component products are obtained and hence considerations of temperature and pressure will vary within a range of conversion levels designed to provide the highest selectivity and maximum yield.

The starting feed materials for the present improved process are olefins of from 2 to 4 carbon atoms, such as, for example, propylene and butylene. The feedstock may be comprised of a single olefin or a mixture of different olefins.

The amount of diluent which may be present in the improved process of this invention is not narrowly critical and may vary within the range of 0 to about 90 weight percent based on the weight of olefin feedstock. Preferably, the amount of diluent is within the range of from about 20 to about 60 weight percent.

The improvement realized by way of the present process is substantial in that coking and aging rates of the catalyst are controlled while conversions remain favorable. The zeolite catalysts above defined for use herein are found to be hydrophobic and unique in their ability to utilize the large molar equivalents of co-fed water to resist coking and aging at the activity levels maintained in the present process.

The following specific examples will serve to illustrate the process of the present invention, without unduly limiting same.

EXAMPLE 1

A silicate solution containing 90.9 pounds Q-brand sodium silicate (8.8 wt. % $Na_2O$, 28.5 wt. % $SiO_2$ and 62.7 wt. % $H_2O$), 52.6 pounds $H_2O$, and 118 grams Daxad 27 dispersant (sodium salt of polymerized substituted benzoid alkylsulfonic acid combined with an inert inoganic suspending agent) was mixed in a mixing nozzle with an acid solution containing 1430 grams $Al_2(SO_4)_3.14\ H_2O$, 3440 grams $H_2SO_4$, 4890 grams NaCl, and 54 pounds $H_2O$ to form a gel which was discharged into a 30 gallon autoclave to which 1180 grams of $H_2O$ had been previously added. The gel was whipped by agitation and 2840 grams of NaCl was added and thoroughly blended. The agitation was stopped and an organic solution containing 2780 grams tri-n-propylamine, 2390 grams n-propyl bromide, and methyl ethyl ketone was added as a layer on top of the gel. The autoclave was sealed and heated to about 220° F. without agitation and held there for 14–15 hours to prereact the organics. At the end of the prereaction period the agitation was commenced at 90 rpm to start the initial crystallization period. After about 75–80 hours, the temperature was raised to 320° F. and held there for about 3 hours to complete crystallization. The excess of unreacted organics were flashed off and the contents of the autoclave were cooled and discharged. Chemical analysis of the washed crystalline product was 2.21 wt. % $Al_2O_3$, 94.9 wt. % $SiO_2$, 0.81 wt. % Na, 0.67 wt. % N, and 8.2 wt. % carbon, and it was identified by X-ray as ZSM-5.

After drying at about 250° F., the zeolite was mixed with alpha-alumina monohydrate and $H_2O$ (65% zeolite, 35% alumina binder on ignited basis), then extruded to form 1/16 inch pellets. The pellets were calcined in nitrogen atmosphere for 3 hours at 1000° F., ion exchanged with 1 Normal $NH_4Cl$ at room temperature for 1 hour using 5 milliliters solution per gram of dry zeolite, water-washed, and finally calcined in 100% air for 3 hours at 1000° F.

EXAMPLE 2

30 grams of the dried ammonium-ZSM-5 extrudate from Example 1 were exchanged at room temperature with 300 milliliters of 10% $AgNO_3$ solution, water washed and then exchanged at room temperature with 500 milliliters of 30% KSCN solution, water-washed, and finally dried at 110° C. Potassium content of the final product was 0.89 wt. %.

EXAMPLE 3–4

A 10 cc quantity of the catalyst material prepared in Example 1 was sized to 14–28 mesh and placed in a 5/16-inch I.D. stainless steel tubing reactor. Temperature exotherms were easily discerned in this reactor because of the thin wall tubing and air space between the tubing and three heater blocks. The flow rate of propylene feedstock to the reactor was monitored through a rotometer (Example 3), and water was introduced at the reactor inlet as required (Example 4). Liquid product at room temperature and gaseous products were measured and then analyzed by gas chromatography and mass spec, respectively.

Detailed data on processing propylene alone (Example 3) for nine days are presented in Table 4; and propylene with 3 moles water diluent per mole of propylene (Example 4) for twelve days in Table 5. All runs were at 700° F. catalyst bed temperature setting, atmospheric pressure, and about 0.8 WHSV propylene. Propylene feed rate was set at 4.5±0.5 grams/hour.

TABLE 4

Propylene Processing Over Catalyst of Example 1

| Days on Stream | 1[1] | 2 | 3 |
|---|---|---|---|
| Catalyst Temp., ° F., Average | 730 | 733 | 733 |
| Hot Spot, ° F. | 794 | 774 | 770 |
| Inches Down Bed (10 In. Bed) | 1 | 1 | 1½ |
| Liquid Product Gravity, ° API | 32.3 | 34.9 | 36.3 |
| Products, wt % | | | |
| Methane | 0.6 | 0.2 | 0.2 |
| $C_2$'s, Total | 1.4 | 0.7 | 0.6 |
| Ethane | 1.4 | 0.7 | 0.6 |
| Ethylene | — | — | — |
| $C_3$'s, Total | 36.4 | 23.7 | 20.5 |
| Propane | 36.2 | 23.3 | 20.0 |
| Propylene | 0.2 | 0.4 | 0.5 |
| $C_4$'s, Total | 24.1 | 26.9 | 27.3 |
| Isobutane | 14.8 | 17.1 | 17.4 |
| n-Butane | 8.8 | 9.1 | 9.0 |
| Butenes | 0.5 | 0.7 | 0.9 |
| $C_5$'s, Total | 7.0 | 9.0 | 10.3 |
| Isopentane | 5.5 | 6.8 | 7.5 |
| n-pentane | 1.2 | 1.7 | 2.2 |
| pentenes | 0.1 | 0.1 | 0.1 |
| Cyclopentane | 0.2 | 0.4 | 0.5 |
| $C_6^+$, Total | 30.4 | 39.4 | 41.0 |
| $C_6$ Non-Aromatics | 0.6 | 1.3 | 2.2 |
| $C_7^+$ Non-Aromatics | 1.7 | 1.2 | 2.0 |
| Benzene | 1.8 | 2.0 | 1.7 |
| Toluene | 9.2 | 10.7 | 9.8 |
| $C_8$ Alkylbenzenes | 10.1 | 12.8 | 12.9 |
| $C_9$ Alkylbenzenes | 4.5 | 6.3 | 7.2 |
| $C_{10}$ Alkylbenzenes | 1.4 | 2.1 | 2.3 |
| $C_{11}$ Alkylbenzenes | 2.5 | 3.0 | 2.9 |
| Total Aromatics | 28.1 | 36.9 | 36.8 |
| Total | 100.0 | 100.0 | 100.0 |
| $C_5^+$, wt % | 37.4 | 48.4 | 51.3 |
| $C_5^+$ Octane No., R+O | — | 101.0 | — |

| Days on Stream | 4 | 5 | 6 |
|---|---|---|---|
| Catalyst Temp., ° F., Average | 738 | 737 | 734 |
| Hot Spot, ° F. | 764 | 761 | 758 |
| Inches Down Bed (10 In. Bed) | 1½ | 1½ | 2 |
| Liquid Product Gravity, ° API | 40.1 | 43.2 | 45.5 |
| Products, wt % | | | |
| Methane | 0.1 | 0.1 | 0.1 |
| $C_2$'s, Total | 0.6 | 0.6 | 0.7 |
| Ethane | 0.5 | 0.3 | 0.2 |
| Ethylene | 0.1 | 0.3 | 0.5 |
| $C_3$'s, Total | 16.9 | 14.5 | 12.0 |
| Propane | 16.3 | 13.4 | 10.4 |
| Propylene | 0.6 | 1.1 | 1.6 |
| $C_4$'s, Total | 27.0 | 25.7 | 25.3 |
| Isobutane | 17.3 | 16.2 | 15.7 |
| n-Butane | 8.4 | 7.5 | 6.5 |
| Butenes | 1.3 | 2.0 | 3.1 |
| $C_5$'s, Total | 11.6 | 11.3 | 12.7 |
| Isopentane | 8.1 | 7.7 | 8.1 |
| n-Pentane | 2.8 | 2.8 | 3.3 |
| Pentenes | 0.1 | 0.3 | 0.7 |
| Cyclopentane | 0.6 | 0.5 | 0.6 |
| $C_6^+$, Total | 43.7 | 47.6 | 49.1 |
| $C_6$ Non-Aromatics | 5.8 | 3.6 | 6.3 |
| $C_7^+$ Non-Aromatics | 3.5 | 3.4 | 12.2 |
| Benzene | 1.2 | 0.8 | 0.6 |
| Toluene | 8.2 | 6.1 | 4.9 |
| $C_8$ Alkylbenzenes | 11.8 | 9.8 | 10.1 |
| $C_9$ Alkylbenzenes | 7.5 | 7.0 | 9.1 |
| $C_{10}$ Alkylbenzenes | 3.0 | 4.2 | 3.4 |
| $C_{11}$ Alkylbenzenes | 2.7 | 2.7 | 2.5 |
| Total Aromatics | 34.4 | 30.6 | 30.6 |
| Total | 100.0 | 100.0 | 100.0 |
| $C_5^+$ wt % | 55.3 | 58.9 | 61.8 |
| $C_5^+$ Octane No., R+O | — | — | — |

| Days on Stream | 7 | 8 | 9 |
|---|---|---|---|
| Catalyst Temp., ° F., Average | 732 | 729 | 729 |
| Hot Spot, ° F. | 758 | 752 | 749 |
| Inches Down Bed (10 In. Bed) | 2 | 2 | 2 |
| Liquid Product Gravity, ° API | 52.3 | 53.6 | 57.4 |
| Products, wt % | | | |
| Methane | <0.1 | <0.1 | <0.1 |
| $C_2$'s, Total | 1.1 | 1.2 | 1.2 |
| Ethane | 0.1 | 0.1 | 0.1 |
| Ethylene | 1.0 | 1.1 | 1.1 |
| $C_3$'s, Total | 9.9 | 9.2 | 9.4 |
| Propane | 6.4 | 5.3 | 4.4 |
| Propylene | 3.5 | 3.9 | 5.0 |
| $C_4$'s, Total | 26.8 | 22.6 | 22.6 |
| Isobutane | 10.7 | 9.2 | 7.5 |
| n-Butane | 5.7 | 5.3 | 5.3 |
| Butenes | 6.4 | 8.1 | 9.8 |
| $C_5$'s, Total | 13.5 | 13.8 | 13.4 |
| Isopentane | 6.9 | 6.1 | 5.2 |
| n-Pentane | 3.9 | 3.8 | 4.1 |
| Pentenes | 2.4 | 3.5 | 4.1 |
| Cyclopentane | 0.3 | 0.4 | 0.3 |
| $C_6^+$, Total | 52.7 | 53.2 | 53.1 |
| $C_6$ Non-Aromatics | 8.4 | 10.1 | 11.8 |
| $C_7^+$ Non-Aromatics | 21.8 | 28.1 | 30.5 |
| Benzene | 0.4 | 0.4 | 0.5 |
| Toluene | 2.6 | 1.4 | 0.8 |
| $C_8$ Alkylbenzenes | 6.5 | 4.0 | 2.5 |
| $C_9$ Alkylbenzenes | 7.7 | 5.5 | 4.0 |
| $C_{10}$ Alkylbenzenes | 3.6 | 2.5 | 2.0 |
| $C_{11}$ Alkylbenzenes | 1.7 | 1.2 | 1.0 |
| Total Aromatics | 22.5 | 15.0 | 10.8 |
| Total | 100.0 | 100.0 | 100.0 |
| $C_5^+$, wt % | 66.2 | 67.0 | 66.8 |
| $C_5^+$ Octane No., R+O | — | 93.8 | — |

[1] First six hours with $H_2O$, 5.2 cc/hr. The data shown corresponds to the 18 hr. balance run.

TABLE 5

Propylene Processing Over Catalyst of Example 1 In Presence of Water

| Days on Stream | 1 | 2 | 3 |
|---|---|---|---|
| $C_3^=$/hr, g | 5.0 | 4.9 | 4.7 |
| $H_2O$/hr, cc | 6.7 | 5.4 | 6.2 |
| Mole Ratio, $H_2O/C_3^=$ | 3.1 | 2.5 | 3.0 |
| Catalyst Temp., ° F., Average | 720 | 719 | 718 |
| Hot Spot, ° F. | 757 | 750 | 746 |
| Inches Down Bed | 1 | 1 | 1 |
| Liquid Product Gravity, ° API | 37.1 | 40.7 | 41.9 |
| Products, wt % | | | |
| Methane | 0.1 | 0.1 | 0.1 |
| $C_2$'s, Total | 1.2 | 1.2 | 1.9 |
| Ethane | 0.4 | 0.3 | 0.4 |
| Ethylene | 0.8 | 0.9 | 1.5 |
| $C_3$'s, Total | 20.3 | 17.9 | 17.4 |
| Propane | 18.8 | 16.2 | 14.8 |
| Propylene | 1.5 | 1.7 | 2.6 |
| $C_4$'s, Total | 30.8 | 29.8 | 29.2 |
| Isobutane | 20.8 | 19.7 | 19.0 |
| n-Butane | 7.7 | 7.6 | 6.6 |
| Butenes | 2.3 | 2.5 | 3.6 |
| $C_5$'s, Total | 9.0 | 9.8 | 10.6 |
| Isopentane | 6.8 | 7.2 | 7.4 |
| n-Pentane | 1.8 | 2.2 | 2.4 |
| Pentenes | 0.2 | 0.3 | 0.6 |
| Cyclopentane | 0.2 | 0.1 | 0.2 |
| $C_6^+$, Total | 38.6 | 31.2 | 40.9 |
| $C_6$ Non-Aromatics | 3.6 | 4.4 | 5.5 |

TABLE 5-continued
Propylene Processing Over Catalyst of Example 1
In Presence of Water

| | | | |
|---|---|---|---|
| C$_7^+$ Non-Aromatics | 1.2 | 2.1 | 3.0 |
| Benzene | 1.8 | 1.6 | 1.2 |
| Toluene | 10.3 | 9.6 | 8.1 |
| C$_8$ Alkylbenzenes | 12.8 | 13.3 | 12.5 |
| C$_9$ Alkylbenzenes | 5.9 | 7.0 | 7.6 |
| C$_{10}$ Alkylbenzenes | 1.2 | 1.3 | 1.5 |
| C$_{11}$ Alkylbenzenes | 1.8 | 1.9 | 1.5 |
| Total Aromatics | 33.8 | 34.7 | 32.4 |
| Total | 100.0 | 100.0 | 100.0 |
| C$_5^+$, wt % | 47.6 | 51.0 | 51.3 |
| C$_5^+$ Octane No., R+O | — | 99.9 | — |

| Days on Stream | 4 | 5 | 6 |
|---|---|---|---|
| C$_3^=$/hr, g | 4.6 | 4.6 | 4.6 |
| H$_2$O/hr, cc | 6.3 | 6.3 | 6.3 |
| Mole Ratio, H$_2$O/C$_3^=$ | 3.2 | 3.2 | 3.2 |
| Catalyst Temp., °F., Average | 718 | 717 | 716 |
| Hot Spot, °F. | 742 | 742 | 738 |
| Inches Down Bed | 1 | 1 | 1 |
| Liquid Product Gravity, °API | 44.0 | 45.1 | 45.2 |
| Products, wt % | | | |
| Methane | 0.1 | 0.1 | 0.1 |
| C$_2$'s, Total | 2.0 | 2.5 | 2.5 |
| Ethane | 0.3 | 0.2 | 0.3 |
| Ethylene | 1.7 | 2.3 | 2.2 |
| C$_3$'s, Total | 16.4 | 15.5 | 15.6 |
| Propane | 13.7 | 11.5 | 11.7 |
| Propylene | 2.7 | 4.0 | 3.9 |
| C$_4$'s, Total | 28.8 | 28.5 | 28.8 |
| Isobutane | 18.3 | 17.0 | 17.4 |
| n-Butane | 6.5 | 5.6 | 5.6 |
| Butenes | 4.0 | 5.9 | 5.8 |
| C$_5$'s, Total | 11.3 | 11.2 | 11.4 |
| Isopentane | 7.7 | 7.1 | 7.2 |
| n-Pentane | 2.7 | 2.6 | 2.7 |
| Pentenes | 0.7 | 1.3 | 1.3 |
| Cyclopentane | 0.2 | 0.2 | 0.2 |
| C$_6^+$, Total | 41.5 | 42.2 | 41.7 |
| C$_6$ Non-Aromatics | 6.3 | 6.8 | 7.0 |
| C$_7^+$ Non-Aromatics | 4.1 | 5.0 | 5.7 |
| Benzene | 1.0 | 0.9 | 0.7 |
| Toluene | 7.3 | 6.6 | 6.0 |
| C$_8$ Alkylbenzenes | 11.9 | 11.6 | 11.0 |
| C$_9$ Alkylbenzenes | 7.9 | 8.2 | 8.2 |
| C$_{10}$ Alkylbenzenes | 1.6 | 1.7 | 1.7 |
| C$_{11}$ Alkylbenzenes | 1.4 | 1.4 | 1.4 |
| Total Aromatics | 31.1 | 30.4 | 29.0 |
| Total | 100.0 | 100.0 | 100.0 |
| C$_5^+$, wt % | 52.5 | 53.1 | 52.7 |
| C$_5^+$ Octane No., R+O | — | 97.9 | — |

| Days on Stream | 7 | 8 | 11 |
|---|---|---|---|
| C$_3^=$/hr, g | 4.4 | 4.0 | 4.9 |
| H$_2$O/hr, cc | 6.5 | 6.3 | 6.5 |
| Mole Ratio, H$_2$O/C$_3^=$ | 3.4 | 3.7 | 3.1 |
| Catalyst Temp., °F., Average | 716 | 717 | 718 |
| Hot Spot, °F. | 738 | 737 | 741 |
| Inches Down Bed | 1 | 1 | 1 |
| Liquid Product Gravity, °API | 46.2 | 46.3 | 47.9 |
| Products, wt % | | | |
| Methane | 0.1 | 0.1 | <0.1 |
| C$_2$'s, Total | 1.9 | 2.0 | 2.4 |
| Ethane | 0.3 | 0.2 | 0.2 |
| Ethylene | 1.6 | 1.8 | 2.2 |
| C$_3$'s, Total | 14.4 | 13.8 | 13.4 |
| Propane | 11.4 | 10.0 | 8.4 |
| Propylene | 3.0 | 3.8 | 5.0 |
| C$_4$'s, Total | 29.6 | 27.9 | 28.8 |
| Isobutane | 17.7 | 15.8 | 14.5 |
| n-Butane | 6.8 | 5.9 | 6.0 |
| Butenes | 5.1 | 6.2 | 8.3 |
| C$_5$'s, Total | 11.8 | 11.6 | 12.7 |
| Isopentane | 7.7 | 7.1 | 6.9 |
| n-Pentane | 2.9 | 2.8 | 3.0 |
| Pentenes | 1.0 | 1.5 | 2.6 |
| Cyclopentane | 0.2 | 0.2 | 0.2 |
| C$_6^+$, Total | 42.4 | 44.7 | 42.8 |
| C$_6$ Non-Aromatics | 7.7 | 7.5 | 8.4 |
| C$_7^+$ Non-Aromatics | 7.6 | 7.6 | 8.8 |
| Benzene | 0.6 | 0.7 | 0.5 |
| Toluene | 5.6 | 5.7 | 4.4 |
| C$_8$ Alkylbenzenes | 10.2 | 10.6 | 8.8 |
| C$_9$ Alkylbenzenes | 7.9 | 8.5 | 7.9 |
| C$_{10}$ Alkylbenzenes | 1.6 | 1.8 | 1.9 |
| C$_{11}$ Alkylbenzenes | 2.2 | 2.3 | 2.1 |
| Total Aromatics | 28.1 | 29.6 | 25.6 |
| Total | 100.0 | 100.0 | 100.0 |
| C$_5^+$, wt % | 53.7 | 55.4 | 54.3 |
| C$_5^+$ Octane No., R+O | — | — | 96.5 |

| Days on Stream | 12 |
|---|---|
| C$_3^=$/hr, g | 4.1 |
| H$_2$O/hr, cc | 3.8 |
| Mole Ratio, H$_2$O/C$_3^=$ | 2.1 |
| Catalyst Temp., °F., Average | 717 |
| Hot Spot, °F. | 753 |
| Inches Down Bed | 1 |
| Liquid Product Gravity, °API | 45.5 |
| Products, wt % | |
| Methane | 0.1 |
| C$_2$'s, Total | 0.8 |
| Ethane | 0.7 |
| Ethylene | 0.1 |
| C$_3$'s, Total | 19.3 |
| Propane | 18.9 |
| Propylene | 0.4 |
| C$_4$'s, Total | 24.9 |
| Isobutane | 15.6 |
| n-Butane | 8.1 |
| Butenes | 1.2 |
| C$_5$'s, Total | 11.1 |
| Isopentane | 7.8 |
| n-Pentane | 3.0 |
| Pentenes | 0.2 |
| Cyclopentane | 0.1 |
| C$_6^+$, Total | 44.0 |
| C$_6$ Non-Aromatics | 7.9 |
| C$_7^+$ Non-Armotatics | 6.5 |
| Benzene | 0.7 |
| Toluene | 5.3 |
| C$_8$ Alkylbenzenes | 9.6 |
| C$_9$ Alkylbenzenes | 8.0 |
| C$_{10}$ Alkylbenzenes | 2.5 |
| C$_{11}$ Alkylbenzenes | 3.5 |
| Total Aromatics | 29.6 |
| Total | 100.0 |
| C$_5^+$, wt % | 54.4 |
| C$_5^+$ Octane No., R+O | — |

In Example 3 the conversion of propylene was essentially complete (>95%) for the entire experiment, with and without water present. Aging was, therefore, indicated by changes in hot spot temperature and/or changes in the composition of the products.

| Temperature Characteristics of Catalyst Bed | | |
|---|---|---|
| | Propylene Alone | 3/1 Water/Propylene |
| 1 Day on Stream | | |
| Hot Spot, °F. | 794 | 757 |
| In. Down Bed (10" Bed) | 1 | 1 |
| Avg. Cat. Temp., °F. | 730 | 720 |
| 8 Days on Stream | | |
| Hot Spot, °F. | 752 | 737 |
| In. Down Bed (10" Bed) | 2 | 1 |
| Avg. Cat. Temp., °F. | 729 | 717 |
| 11 Days on Stream | | |
| Hot Spot, °F. | — | 741 |
| In. Down Bed (10" Bed) | — | 1 |
| Avg. Cat. Temp., °F. | — | 718 |

The presence of water decreased the observed temperature of the hot spot and also the average temperature of the catalyst bed. As shown below water had a very pronounced effect on rate of coke deposition.

|  | Propylene | Propylene + Water |
|---|---|---|
| Catalyst Age, Days | 9 | 12 |
| Coke on Catalyst, wt % | 21.4 | 9.19 |
| Reg. Cat. Surface Area, $m^2/g$ | 331 | 328 |

On the twelfth day the mole ratio of $H_2O/C_3^=$ was decreased from 3/1 to 2/1 (Table 5), resulting in an increase in the hot spot from 741° to 753° F. and a slight reversal of the small aging trend in product composition.

Fresh catalyst aromatic selectivity is related to hot spot temperature. Aromatic selectivity is initially highest (37%) for propylene alone, but winds up lowest (22%) after seven days on stream. On the other hand, water diluent showed lower decay rate in aromatic selectivity. Also the water experiment showed lower $C_{10}+C_{11}$ aromatic/total aromatic ratio. It thus appears that water is contributing something more than merely removing heat.

Octane number (R+O) correlates with aromatic make, i.e., was highest initially (101) charging propylene alone, then dropped off so that after about seven days it was the lowest (93.8). When processing in the presence of the large molar equivalents of co-fed water, octane number started out (at the second day) at about 100 and only dropped to 96.5 after a full 11 days on stream.

Liquid products from runs of Example 3 at both initial and nine-eleven days on stream were analyzed for conjugated diolefins by refluxing with maleic anhydrids in toluene solution, unreacted anhydride titrating and reporting results as millimoles conjugated diolefin per gram of sample.

| | Conjugated Diolefin Content of Liquid Products | | | |
|---|---|---|---|---|
| | Propylene Alone | | Propylene/ Water | |
| Days on Stream | 1 | 9 | 1 | 11 |
| Liquid Product Mol wt | 100.6 | 97.7 | 97.7 | 97.7 |
| Conjugated Diolefins | | | | |
| Millemoles/g Sample | 0.056 | 0.139 | 0.023 | 0.024 |
| Moles/Mole Sample | 0.006 | 0.014 | 0.002 | 0.002 |

| | Conjugated Diolefin Content of Liquid Products | | | |
|---|---|---|---|---|
| | Propylene Alone | | Propylene/ Water | |
| Days on Stream | 1 | 9 | 1 | 11 |
| Mole % | 0.06 | 1.4 | 0.2 | 0.2 |

From this information it appears that the presence of large amounts of water inhibits diolefin formation, particularly with an aged catalyst.

EXAMPLES 5-6

In these examples a blend of 8 weight % propylene, 12 weight % butylene and 80 weight % propane (diluent) was charged as a liquid (Example 5) to the reactor from a positive displacement pump (BIF) at 400 psig. Water was also charged from a BIF pump through a separate line to the head of the reactor when required for Example 6.

The catalyst bed for both examples consisted of 0.8 cc 12-25 mesh catalyst from Example 2 (KZSM-5 extrudate, 0.89% K) mixed with 7.2 cc alumina to provide a bed length of 9-1/2-inches in the 9/32-inch I.D. stainless steel tubing reactor. The bed was pretreated in situ with flowing gas (air or $H_2$) at 950° F. for 2 hours. No hot spot was observed during the runs in this "pseudo-isothermal" reactor.

The product stream was reduced to atmospheric pressure by a grove loader, and the gas and liquid products were analyzed by mass spectrometry and gas chromatography.

Run data without (Example 5) and with co-fed water (Example 6) are in Tables 6 and 7, respectively. Standard conditions were 400 psig, 1.2-1.3 WHSV olefin (on KZSM-5 extrudate) and start-of-run temperature of about 550° F. In the co-fed water run (Example 6), the WHSV of $H_2O$ (on KZSM-5 extrudate) was 1.3-1.8 and the mole ratio of $H_2O$/olefin was 2.7-4.1.

Figure 1:
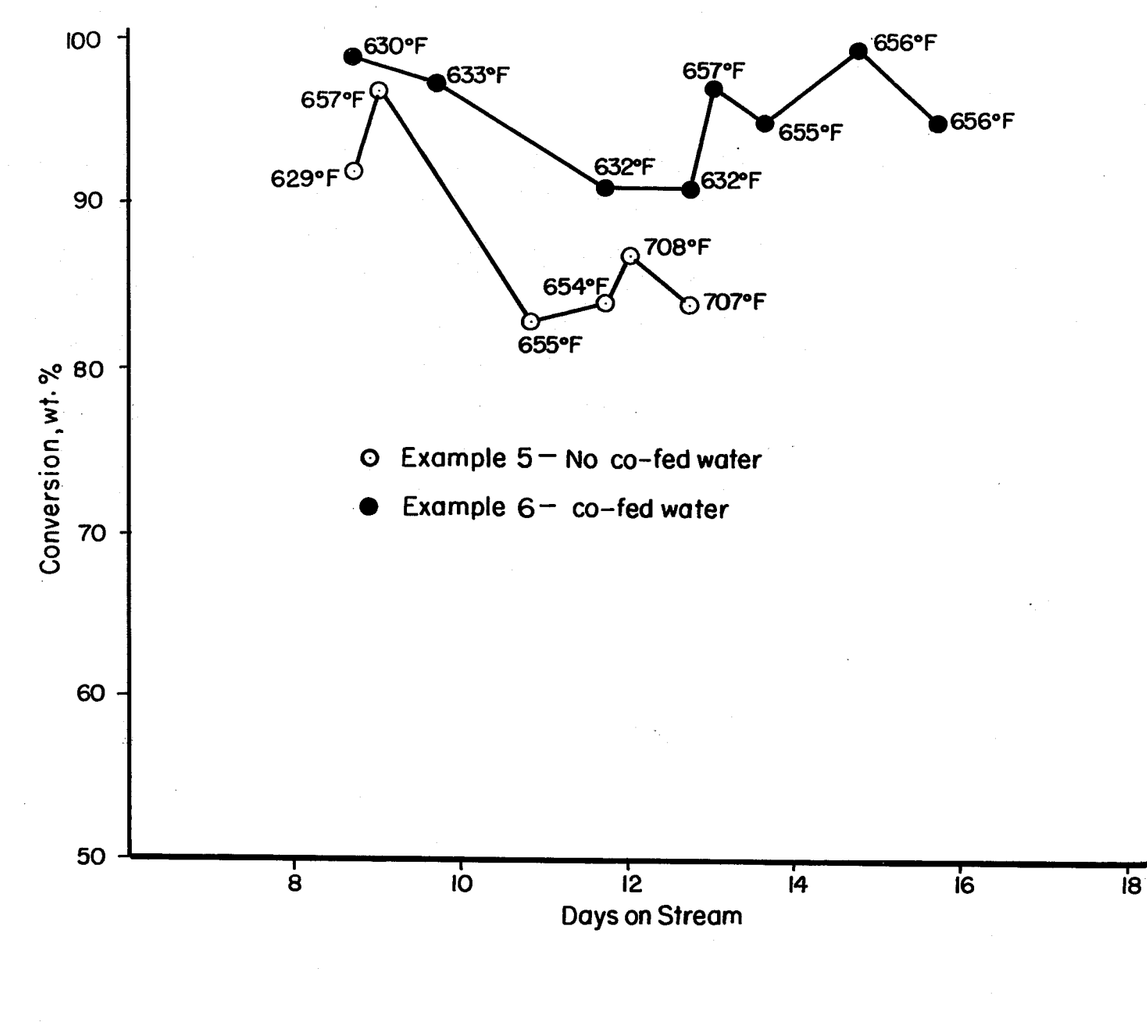
The FIGURE is a comparative plot of propylene conversion (wt. %) versus process time on stream (days) for the data generated by specific examples 5 and 6, presented hereinafter.

Conversion of olefin feedstock in wt. % for Examples 5 and 6 are plotted against process time on stream in days in the Figure. This "aging plot" shows that with co-fed water the olefin feedstock conversion stabilized at about 95 wt. % between about 13 and 16 days on stream at only about 650° F. The "aging plot" further shows by way of comparison that without co-fed water in the same process, olefin conversion dropped to a level of about 85 wt. % at about 13 days on stream, requiring a temperature of about 700° F.

TABLE 6

| | Olefin Processing Over Catalyst of Example 2 | | | | | | | |
|---|---|---|---|---|---|---|---|---|
| Days on Stream | 0.8 | 2.9 | 3.7 | 4.7 | 5.7 | 6.7 | 7.7 | 8.7 |
| Temp., ° F., Average | 556 | 555 | 555 | 556 | 557 | 603 | 630 | 629 |
| WHSV, Total | 6.36 | 6.00 | 5.88 | 6.09 | 6.27 | 6.35 | 6.38 | 6.51 |
| Olefin Only | 1.27 | 1.20 | 1.17 | 1.22 | 1.25 | 1.27 | 1.28 | 1.30 |
| Total Charge, Accumulative g per g KZSM-5 Ext. | 114 | 424 | 542 | 687 | 837 | 986 | 1138 | 1294 |
| Olefin Conversion, Total Wt. % | 90 | 85 | 70 | 52 | 59 | 76 | 82 | 79 |
| $C_3^=$, wt % | 99 | 96 | 83 | 62 | 69 | 88 | 95 | 92 |
| $C_4^=$, wt % | 77 | 68 | 50 | 38 | 44 | 57 | 63 | 59 |
| Yields, Wt % (Propane Free) | | | | | | | | |
| $C_1$ | — | — | — | — | — | — | — | — |
| $C_2$'s Total | 1.5 | 0.7 | 0.8 | 1.2 | 0.8 | 0.8 | 0.8 | 0.7 |
| $C_2^=$ | 1.5 | 0.7 | 0.8 | 1.2 | 0.8 | 0.8 | 0.8 | 0.7 |
| $C_2$ | — | — | — | — | — | — | — | — |
| $C_3^=$ | 0.1 | 2.5 | 10.5 | 23.0 | 18.5 | 7.1 | 3.2 | 4.8 |
| $C_4$'s Total | 16.2 | 14.6 | 22.3 | 26.6 | 24.0 | 20.0 | 18.4 | 18.9 |
| i-$C_4$ | 6.9 | 1.9 | 2.5 | 1.7 | 1.1 | 2.7 | 3.2 | 2.0 |
| $C_4^=$ | — | — | — | — | 0.4 | — | 0.4 | 0.4 |
| $C_5$'s Total | 19.9 | 11.1 | 10.8 | 8.0 | 9.0 | 12.3 | 17.3 | 17.2 |
| i-$C_5$ | 5.3 | 0.8 | 0.8 | 0.9 | 0.4 | — | 1.2 | 0.8 |

TABLE 6-continued

Olefin Processing Over Catalyst of Example 2

| | | | | | | | | |
|---|---|---|---|---|---|---|---|---|
| $C_5^=$ | 14.6 | 10.3 | 10.0 | 7.1 | 2.6 | 11.5 | 16.1 | 15.7 |
| n-$C_5$ | — | — | — | — | — | 0.8 | — | 0.7 |
| $C_6^+$ | 62.3 | 71.1 | 55.4 | 41.2 | 47.7 | 59.8 | 60.3 | 58.4 |
| | 100.0 | 100.0 | 100.0 | 100.0 | 100.0 | 100.0 | 100.0 | 100.0 |
| $C_4^+$, wt % | 98.4 | 96.8 | 88.7 | 75.8 | 80.7 | 92.1 | 96.0 | 94.5 |
| $C_5^+$, wt % | 82.2 | 82.2 | 66.2 | 49.2 | 56.7 | 72.1 | 77.6 | 75.6 |
| Liquid Product, 90% B.P., °F. | | 386 | | | 392 | | 405 | |
| Liquid Product Octane Number, R+O | | 86.3 | | | — | | 83.5 | |
| Days on Stream | 9.0 | 10.8 | 11.7 | 12.0 | 12.7 | | | |
| Temp., °F., Average | 657 | 655 | 654 | 708 | 707 | | | |
| WHSV, Total | 6.44 | 6.54 | 6.04 | 6.10 | 6.32 | | | |
| Olefin Only | 1.29 | 1.31 | 1.21 | 1.22 | 1.26 | | | |
| Total Charge, Accumulative g per g KZSM-5 Ext. | 1312 | 1611 | 1752 | 1794 | 1902 | | | |
| Olefin Conversion, Total Wt. % | 82 | 70 | 72 | 70 | 71 | | | |
| $C_3^=$, wt % | 97 | 83 | 84 | 87 | 84 | | | |
| $C_4^=$, wt % | 59 | 51 | 54 | 45 | 52 | | | |
| Yields, Wt % (Propane Free) | | | | | | | | |
| $C_1$ | — | — | — | — | — | | | |
| $C_2$'s Total | 0.9 | 0.8 | 0.8 | 0.3 | 0.9 | | | |
| $C_2^=$ | 0.9 | 0.8 | 0.8 | 0.3 | 0.9 | | | |
| $C_2$ | — | — | — | — | — | | | |
| $C_3^=$ | 1.8 | 10.4 | 9.6 | 7.9 | 9.6 | | | |
| $C_4$'s Total | 19.2 | 22.8 | 22.0 | 31.6 | 26.8 | | | |
| i-$C_4$ | 2.4 | 2.8 | 3.7 | 9.8 | 6.5 | | | |
| $C_4^=$ | 16.5 | 19.6 | 18.3 | 21.8 | 19.4 | | | |
| n-$C_4$ | 0.3 | 0.4 | — | — | 0.9 | | | |
| $C_5$'s Total | 19.5 | 16.2 | 16.8 | 20.0 | 17.3 | | | |
| i-$C_5$ | 1.2 | 1.7 | 3.2 | 3.8 | 4.0 | | | |
| $C_5^=$ | 18.0 | 14.5 | 13.6 | 16.2 | 13.3 | | | |
| n-$C_5$ | 0.3 | — | — | — | — | | | |
| $C_6^+$ | 58.6 | 49.8 | 50.8 | 40.2 | 45.4 | | | |
| | 100.0 | 100.0 | 100.0 | 100.0 | 100.0 | | | |
| $C_4^+$, wt % | 97.3 | 88.8 | 89.6 | 91.8 | 89.5 | | | |
| $C_5^+$, wt % | 78.1 | 66.0 | 67.6 | 60.2 | 62.7 | | | |
| Liquid Product, 90% B.P., °F. | | 401 | | | 416 | | | |
| Liquid Product Octane Number, R+O | | 83.7 | | | — | | | |

TABLE 7

Olefin Processing Over Catalyst of Example 2 In Presence of Water

| | | | | | | | | |
|---|---|---|---|---|---|---|---|---|
| Days on Stream | 0.7 | 1.7 | 2.7 | 3.7 | 5.7 | 6.7 | 7.7 | 8.7 |
| Temp., °F., Average | 521 | 553 | 554 | 553 | 554 | 606 | 631 | 630 |
| WHSV, Total Hydrocarbon | 5.78 | 6.12 | 6.37 | 6.45 | 6.33 | 6.41 | 6.01 | 6.04 |
| Olefin Only | 1.16 | 1.22 | 1.27 | 1.29 | 1.27 | 1.22 | 1.20 | 1.21 |
| $H_2O$ | 1.76 | 1.27 | 1.35 | 1.38 | 1.41 | 1.49 | 1.57 | 1.62 |
| Mole Ratio of $H_2O$/Olefin | 4.1 | 2.7 | 2.8 | 2.9 | 2.9 | 3.1 | 3.5 | 3.6 |
| Total HC Charge, Accumulative, g per g KZSM-5 extrudate | 98 | 240 | 388 | 556 | 837 | 1003 | 1152 | 1297 |
| Olefin Conversion, Total, wt. % | 90 | 65 | 46 | 40 | 34 | 76 | 63 | 84 |
| $C_3^=$, wt % | 98 | 84 | 55 | 50 | 42 | 91 | 80 | 99 |
| $C_4$ , wt % | 78 | 37 | 32 | 26 | 22 | 54 | 50 | 62 |
| Yields, wt % (Propane Free) | | | | | | | | |
| $C_1$ | — | — | — | — | — | — | — | — |
| $C_2$'s Total | 0.3 | — | — | — | 0.4 | — | — | — |
| $C_2$ | 0.3 | — | — | — | 0.4 | — | — | — |
| $C_2$ | — | — | — | — | — | — | — | — |
| $C_3^=$ | 1.3 | 15.4 | 25.9 | 30.2 | 34.8 | 5.1 | 11.8 | 0.1 |
| $C_4$'s Total | 7.7 | 26.4 | 27.0 | 29.6 | 33.0 | 19.9 | 24.4 | 16.3 |
| i-$C_4$ | 1.8 | 1.1 | — | — | 1.7 | 0.8 | 3.3 | — |
| $C_4^=$ | 5.9 | 25.3 | 27.0 | 29.6 | 31.3 | 18.6 | 19.9 | 14.7 |
| n-$C_4$ | — | — | — | — | — | 0.5 | 1.2 | 1.6 |
| $C_5$'s Total | 7.3 | 12.3 | 9.1 | 2.0 | 5.9 | 16.3 | 14.1 | 12.4 |
| i-$C_5$ | 0.7 | 1.6 | 1.3 | 0.9 | 0.4 | 2.3 | 2.0 | 3.4 |
| $C_5^=$ | 6.6 | 10.7 | 7.8 | 7.1 | 5.5 | 14.0 | 11.3 | 14.0 |
| n-$C_5$ | — | — | — | — | — | — | 0.8 | — |
| $C_6^+$ | 83.4 | 45.9 | 38.0 | 32.2 | 25.9 | 58.7 | 49.7 | 66.2 |
| | 100.0 | 100.0 | 100.0 | 100.0 | 100.0 | 100.0 | 100.0 | 100.0 |
| $C_4^+$, wt % | 98.4 | 84.6 | 71.1 | 69.8 | 64.8 | 94.9 | 83.2 | 99.9 |
| $C_5^+$, wt % | 90.7 | 58.2 | 47.1 | 40.2 | 31.8 | 75.0 | 63.8 | 83.6 |
| Liquid Product, 90% B.P., °F. | | | 419 | | | | 379 | |
| Liquid Product Octane Number, R+O | | | 85.9 | | | | 87.4 | |
| Days on Stream | 9.7 | 11.7 | 12.7 | 13.0 | 13.6 | 14.7 | 15.7 | |
| Temp., °F., Average | 633 | 632 | 632 | 657 | 655 | 656 | 656 | |
| WHSV, Total Hydrocarbon | 6.11 | 6.25 | 6.24 | 4.42 | 6.15 | 6.23 | 6.24 | |
| Olefin Only | 1.22 | 1.25 | 1.25 | 1.28 | 1.23 | 1.25 | 1.25 | |

TABLE 7-continued

| | Olefin Processing Over Catalyst of Example 2 In Presence of Water | | | | | | |
|---|---|---|---|---|---|---|---|
| $H_2O$ | 1.70 | 1.73 | 1.76 | 1.78 | 1.76 | 1.76 | 1.76 |
| Mole Ratio of $H_2O$/Olefin | 3.6 | 3.7 | 3.8 | 3.7 | 3.8 | 3.8 | 3.8 |
| Total HC Charge, Accumulative, g per g KZSM-5 extrudate | 1438 | 1733 | 1880 | 1921 | 2023 | 2172 | 2323 |
| Olefin Conversion, Total, Wt. % | 81 | 77 | 75 | 79 | 78 | 80 | 78 |
| $C_3^=$, wt % | 97 | 91 | 91 | 97 | 95 | 99 | 95 |
| $C_4$, wt. % | 57 | 55 | 51 | 51 | 52 | 68 | 52 |
| Yields, wt % (Propane Free) | | | | | | | |
| $C_1$ | — | — | — | — | — | — | — |
| $C_2$'s Total | — | 0.4 | — | — | — | 0.3 | — |
| $C_2$ | — | — | — | — | — | — | — |
| $C_2^=$ | — | 0.4 | — | — | — | 0.3 | — |
| $C_3$ | 1.7 | 5.3 | 5.2 | 1.6 | 3.2 | 0.1 | 3.3 |
| $C_4$'s Total | 18.5 | 20.6 | 25.0 | 22.9 | 21.3 | 17.6 | 23.3 |
| i-$C_4$ | 0.5 | 2.2 | 5.6 | 3.2 | 1.3 | 3.7 | 3.8 |
| $C_4^=$ | 17.1 | 18.0 | 19.4 | 19.7 | 19.1 | 12.7 | 19.1 |
| n-$C_4$ | 0.9 | 0.4 | — | — | 0.9 | 1.2 | 0.4 |
| $C_5$'s Total | 19.2 | 14.5 | 15.7 | 17.2 | 18.8 | 17.1 | 15.3 |
| i-$C_5$ | 3.1 | 1.9 | 1.7 | 2.3 | 2.3 | 3.3 | 1.7 |
| $C_5^=$ | 16.1 | 12.6 | 14.0 | 14.9 | 16.5 | 13.4 | 13.6 |
| n-$C_5$ | — | — | — | — | — | 0.4 | — |
| $C_6^+$ | 60.6 | 59.2 | 54.1 | 58.3 | 56.7 | 64.9 | 58.1 |
| | 100.0 | 100.0 | 100.0 | 100.0 | 100.0 | 100.0 | 100.0 |
| $C_4^+$, wt % | 98.3 | 94.3 | 94.8 | 98.4 | 96.8 | 97.6 | 96.7 |
| $C_5^+$, wt % | 79.8 | 73.7 | 69.8 | 75.5 | 75.5 | 80.0 | 73.4 |
| Liquid Product, 90% B.P., °F. | | 380 | | | 404 | | |
| Liquid Product Octane Number, R+O | | 87.6 | | | 88.1 | | |

What is claimed is:

1. In a catalytic process for converting olefin feedstock comprising at least one olefin of from 2 to 4 carbon atoms to gasoline components, the improvement which comprises contacting said olefin feedstock with a catalyst comprising a crystalline aluminosilicate zeolite, characterized by a silica/alumina mole ratio of at least 12 and a constraint index within the approximate range of 1 to 12, in the presence of from 0.5 to about 15 moles of water/mole of olefin feedstock, said contacting at a temperature of from about 450° F. to about 800° F. a pressure of from about atmospheric to about 1000 psig and a weight hourly space velocity of from about 0.2 $hr^{-1}$ to about 20 $hr^{-1}$.

2. The process of claim 1 wherein said crystalline aluminosilicate zeolite is ZSM-5.

3. The process of claim 1 wherein said crystalline aluminosilicate zeolite is ZSM-11.

4. The process of claim 1 wherein said crystalline aluminosilicate zeolite is ZSM-12.

5. The process of claim 1 wherein said crystalline aluminosilicate zeolite is ZSM-35.

6. The process of claim 1 wherein said crystalline aluminosilicate zeolite is ZSM-38.

7. The process of claim 1 wherein said olefin feedstock contains a diluent selected from the group consisting of $C_1$-$C_4$ paraffins and hydrogen sulfide.

8. The process of claim 2 wherein said olefin feedstock contains a diluent selected from the group consisting of $C_1$-$C_4$ paraffins and hydrogen sulfide.

9. The process of claim 3 wherein said olefin feedstock contains a diluent selected from the group consisting of $C_1$-$C_4$ paraffins and hydrogen sulfide.

10. The process of claim 4 wherein said olefin feedstock contains a diluent selected from the group consisting of $C_1$-$C_4$ paraffins and hydrogen sulfide.

11. The process of claim 5 wherein said olefin feedstock contains a diluent selected from the group consisting of $C_1$-$C_4$ paraffins and hydrogen sulfide.

12. The process of claim 6 wherein said olefin feedstock contains a diluent selected from the group consisting of $C_1$-$C_4$ paraffins and hydrogen sulfide.

13. The process of claim 1 wherein said mole ratio of water/olefin feedstock is from about 0.5 to about 5.

14. The process of claim 2 wherein said mole ratio of water/olefin feedstock is from about 0.5 to about 5.

15. The process of claim 3 wherein said mole ratio of water/olefin feedstock is from about 0.5 to about 5.

16. The process of claim 4 wherein said mole ratio of water/olefin feedstock is from about 0.5 to about 5.

17. The process of claim 5 wherein said mole ratio of water/olefin feedstock is from about 0.5 to about 5.

18. The process of claim 6 wherein said mole ratio of water/olefin feedstock is from about 0.5 to about 5.

19. The process of claim 7 wherein said mole ratio of water/olefin feedstock is from about 0.5 to about 5.

20. The process of claim 8 wherein said mole ratio of water/olefin feedstock is from about 0.5 to about 5.

21. The process of claim 9 wherein said mole ratio of water/olefin feedstock is from about 0.5 to about 5.

22. The process of claim 10 wherein said mole ratio of water/olefin feedstock is from about 0.5 to about 5.

23. The process of claim 11 wherein said mole ratio of water/olefin feedstock is from about 0.5 to about 5.

24. The process of claim 12 wherein said mole ratio of water/olefin feedstock is from about 0.5 to about 5.

25. The process of claim 1 wherein said olefin feedstock comprises propylene.

26. The process of claim 2 wherein said olefin feedstock comprises propylene.

27. The process of claim 3 wherein said olefin feedstock comprises propylene.

28. The process of claim 4 wherein said olefin feedstock comprises propylene.

29. The process of claim 5 wherein said olefin feedstock comprises propylene.

30. The process of claim 6 wherein said olefin feedstock comprises propylene.

31. The process of claim 7 wherein said olefin feedstock comprises propylene.

32. The process of claim 8 wherein said olefin feedstock comprises propylene.

33. The process of claim 9 wherein said olefin feedstock comprises propylene.

34. The process of claim 10 wherein said olefin feedstock comprises propylene.

35. The process of claim 11 wherein said olefin feedstock comprises propylene.

36. The process of claim 12 wherein said olefin feedstock comprises propylene.

37. The process of claim 1 wherein said olefin feedstock comprises a mixture of propylene and butylene.

38. The process of claim 2 wherein said olefin feedstock comprises a mixture of propylene and butylene.

39. The process of claim 3 wherein said olefin feedstock comprises a mixture of propylene and butylene.

40. The process of claim 4 wherein said olefin feedstock comprises a mixture of propylene and butylene.

41. The process of claim 5 wherein said olefin feedstock comprises a mixture of propylene and butylene.

42. The process of claim 6 wherein said olefin feedstock comprises a mixture of propylene and butylene.

43. The process of claim 7 wherein said olefin feedstock comprises a mixture of propylene and butylene.

44. The process of claim 8 wherein said olefin feedstock comprises a mixture of propylene and butylene.

45. The process of claim 9 wherein said olefin feedstock comprises a mixture of propylene and butylene.

46. The process of claim 10 wherein said olefin feedstock comprises a mixture of propylene and butylene.

47. The process of claim 11 wherein said olefin feedstock comprises a mixture of propylene and butylene.

48. The process of claim 12 wherein said olefin feedstock comprises a mixture of propylene and butylene.

* * * * *

UNITED STATES PATENT AND TRADEMARK OFFICE
CERTIFICATE OF CORRECTION

PATENT NO. : 4,150,062
DATED : April 17, 1979
INVENTOR(S) : William E. Garwood, Philip D. Caesar and James A. Brennan It is certified that error appears in the above-identified patent and that said Letters Patent are hereby corrected as shown below:

Column 15-16, Table 6:  For $C_4=$ the figures should be --
9.3   12.7   20.0   24.9   22.5   17.3   14.8   16.5 -- n-C4 was omitted after $C_4=$

The figures for n-$C_4$ were given for $C_4=$

Column 17-18, Table 7:
Line 15, $C_2$ should be -- $C_2=$ --

Column 19-20, Table 7 (continued):
Line 11, $C_2$ should be -- $C_2=$ --

Signed and Sealed this

Eleventh Day of December 1979

[SEAL]

Attest:

SIDNEY A. DIAMOND

Attesting Officer  Commissioner of Patents and Trademarks